United States Patent
Jo et al.

(10) Patent No.: US 6,277,652 B1
(45) Date of Patent: Aug. 21, 2001

(54) COLORIMETRIC SENSOR EMPLOYING POLYDIACETYLENE MEMBRANE

(75) Inventors: Yoshio Jo, Chiba-ken; Toshiki Inoue, Kashiwa; Kouichi Takada, Fujinomiya, all of (JP)

(73) Assignee: Hogy Medical Co., Ltd., Tokyo (JP)

( * ) Notice: Subject to any disclaimer, the term of this patent is extended or adjusted under 35 U.S.C. 154(b) by 0 days.

(21) Appl. No.: 09/220,389

(22) Filed: Dec. 23, 1998

(30) Foreign Application Priority Data

Dec. 26, 1997 (JP) .................................................. 9-369574

(51) Int. Cl.$^7$ ........................ G01N 21/00; G01N 33/563; G01N 33/543; C12M 1/00; A61K 38/00

(52) U.S. Cl. ................. 436/518; 436/164; 436/512; 436/805; 436/829; 436/905; 435/7.1; 435/287.1; 435/287.2; 435/287.9; 435/808; 435/969; 530/300; 424/143.1

(58) Field of Search ...................... 436/164, 512, 436/518, 805, 829, 905; 435/7.1, 287.1, 287.2, 287.9, 808, 969; 530/300; 424/143.1

(56) References Cited

U.S. PATENT DOCUMENTS

| | | |
|---|---|---|
| 4,195,057 | 3/1980 | Patel . |
| 4,735,745 | 4/1988 | Preziosi et al. . |
| 4,815,843 * | 3/1989 | Teifenthaler et al. ............... 356/128 |
| 4,906,550 * | 3/1990 | Shimanoe et al. .................... 430/260 |
| 5,071,248 * | 12/1991 | Tiefenthaler et al. ............... 356/128 |
| 5,207,862 * | 5/1993 | Baker et al. .......................... 156/600 |

(List continued on next page.)

FOREIGN PATENT DOCUMENTS

| | | |
|---|---|---|
| WO 98/39632 | 9/1998 | (WO) . |
| WO 99/10743 | 3/1999 | (WO) . |

OTHER PUBLICATIONS

"A litmus test' for molecular recognition using artificial membranes," by Charych et al., Chemistry & Biology 1996, vol. 3, No. 2.

(List continued on next page.)

Primary Examiner—Christopher L. Chin
Assistant Examiner—Pensee T. Do
(74) Attorney, Agent, or Firm—Fay, Sharpe, Fagan, Minnich & McKee, LLP

(57) ABSTRACT

Disclosed is a colorimetric sensor comprising polydiacetylene membrane liposomes, a polydiacetylene membrane film or fine particles coated with a polydiacetylene membrane, in which the polydiacetylene membrane is incorporated with a protein having a reduced molecular weight low enough not to cause color change in the polydiacetylene membrane. The examples of the reduced-molecular-weight proteins include an antibody Fab' fragment, an antigenic protein of molecular weight of 100,000 or less, and a peptide consisting of 3–20 amino acid residue, which undergo an antigen-antibody reaction with an antigen or antibody contained in a sample. As the reduced-molecular-weight protein is also employed a combination of single-stranded DNA of 100 bases or less which hybridizes with single-stranded DNA contained in a sample to form a double-stranded DNA, and an antibody which reacts with said double-stranded DNA but does not react with the single-stranded DNA contained in the sample. A method for analysis of biosample is also disclosed, which comprises contacting the colorimetric sensor with a solution sample and utilizing an absorption measurement or a visual observation with the naked eye to detect color change in the polydiacetylene membrane.

1 Claim, 2 Drawing Sheets

U.S. PATENT DOCUMENTS

| | | | | |
|---|---|---|---|---|
| 5,427,915 | * | 6/1995 | Ribi et al. | 435/7.92 |
| 5,451,433 | * | 9/1995 | Frazier et al. | 427/508 |
| 5,540,828 | * | 7/1996 | Yacynych | 204/418 |
| 5,622,872 | * | 4/1997 | Ribi | 436/518 |
| 5,672,465 | * | 9/1997 | Patel et al. | 430/332 |
| 5,853,744 | * | 12/1998 | Mooradian et al. | 424/422 |

OTHER PUBLICATIONS

"Polymerized Liposomes Containing C–Glycosides of Sialic Acid: Potent Inhibitors of Influenza Virus in Vitro Infectivity" J. Am. Chem. Soc. 1993, 115, 1146–47.

"The conformation of membranes" by Reinhard Lipowsky, NATURE, vol. 349, Feb. 7, 1991, pp. 475–481.

"Direct Colorimetric Detection of a Receptor–Ligand Interaction by a Polymerized Bilayer Assembly" by Charych et al., Science, vol. 261, Jul. 30, 1993, pp. 585–588.

Shimizu, et al., "Analysis of a Human Immunodeficiency Virus Type 1 Isolate Carrying a Truncated Transmembrane Glycoprotein, " *Virology,* vol. 189, pp. 534–546 (1992).

* cited by examiner

SEQUENCE LISTING

<160> NUMBER OF SEQ ID NOS: 3

<210> SEQ ID NO 1
<211> LENGTH: 21
<212> TYPE: PRT
<213> ORGANISM: HIV envelope protein (gp 120)
<313> RELEVANT RESIDUES: FROM 254 TO 274

<400> SEQUENCE: 1

Cys Thr His Gly Ile Arg Pro Val Val Ser Thr Gln Leu Leu Leu
1               5                   10                  15

Asn Gly Ser Leu Ala Glu
            20

<210> SEQ ID NO 2
<211> LENGTH: 20
<212> TYPE: DNA
<213> ORGANISM: Probe DNA

<400> SEQUENCE: 2
tatgcttccg gctcgtatgt                                            20

<210> SEQ ID NO 3
<211> LENGTH: 20
<212> TYPE: DNA
<213> ORGANISM: Probe DNA (complementary)

<400> SEQUENCE: 3
atacgaaggc cgagcataca                                            20

COLORIMETRIC SENSOR EMPLOYING POLYDIACETYLENE MEMBRANE

FIELD OF THE INVENTION

The present invention relates to a technique for analyzing different ligands (analytes) in biosamples, and more specifically relates to a novel colorimetric sensor comprising a polydiacetylene membrane and an analysis method which employs the sensor.

BACKGROUND OF THE INVENTION

Membranes formed by self-assembling of amphipathic (amphiphilic) diacetylene molecules exhibit a blue color when polymerized with UV (ultraviolet) irradiation, and such polydiacetylene membranes are known to undergo a change in color to red by the effects of pH, temperature increase, mechanical stress, etc. (see for example, Lipowsky, R. (1991) Nature 349, 475–481; Bloor, D. and Chance, R. R. (1985) Polydiacetylenes: NATO ASI Series E, Applied Science).

Recently, applications of polydiacetylene membranes as biosensors utilizing this property have been proposed (Charych, D. H. et al., (1993) Science 261, 585–588; Reichert, A. et al., (1995) J. Am. Chem. Soc. 115, 1146–1147 (1995); Charych D. H. et al., (1996) Chemistry & Biology 3, 113–120 (1996)). In particular, attempts have been made to construct biosensors in such a manner that the receptors which react specifically with pathogenic bacteria, viruses, toxins and the like present in biosamples are incorporated into polydiacetylene membranes, and the color change (blue to red) induced when the receptors bind to their specific ligands (pathogenic bacteria, viruses, toxins, etc.) is utilized to allow detection of the ligands with high sensitivity. To date, only saccharides and lipids have been used as the receptors in such proposed methods.

Such methods, however, can only be applied to the detection of ligands wherein the binding structure of the receptor and ligand is known and the receptor has been identified. Therefore a number of receptors must be synthesized which is equivalent to the number of types of ligands to be detected, presenting the likely insurmountable difficulty that the conditions for preparation of the polydiacetylene membrane must be determined for the respective cases. Many receptors consisting of saccharides and lipids are highly complicated and difficult to synthesize, while the color change for detection of the ligand is often insufficient. In the method of Charych, et. al. (Chemistry & Biology 3, 113–119 (1996)), for example, gangliosides are incorporated as the receptors for detection of the influenza virus. Because of insufficient color change of the polydiacetylene membrane upon binding between the polydiacetylene membrane and the influenza virus, however, it is necessary to introduce sialic acid into the polydiacetylene at a few percent as a structural change promoter. This complicates the process for preparation of the membrane as a sensor. When the ligands to be detected are different, other types of substances for promoting the structural change must be designed.

In addition, the conventional methods are generally only effective for ligands for which the receptors have molecular weight of about 1000 or less, and the methods are not suitable for detecting ligands which bind to macromolecular receptors. This is because the macromolecular receptors cause color changes in polydiacetylene membranes by simply being incorporated therein.

SUMMARY OF THE INVENTION

It is an object of the present invention to provide a new analysis system utilizing polydiacetylene membranes for analyzing a variety of biosamples in a simple yet highly sensitive manner, wherein the preparation of the membranes is facilitated.

The present inventors were led to the present invention by the finding that the abovementioned object can be attained by incorporating into a polydiacetylene membrane a relatively low molecular weight protein capable of reaction or interaction with a ligand (analyte) in a biosample.

Thus, the present invention provides a colorimetric sensor characterized by comprising polydiacetylene membrane liposomes, a polydiacetylene membrane film or fine particles coated with a polydiacetylene membrane, in which said polydiacetylene membrane is incorporated with a protein having a reduced molecular weight low enough not to cause color change in the polydiacetylene membrane.

In a preferred embodiment, the reduced-molecular-weight protein in the colorimetric sensor of the invention is an antibody Fab' fragment which undergoes an antigen-antibody reaction with an antigen contained in a sample. In another preferred embodiment, the reduced-molecular-weight protein in the colorimetric sensor of the invention is an antigenic protein of molecular weight of 100,000 or less which undergoes an antigen-antibody reaction with an antibody contained in a sample. In still another preferred embodiment, the reduced-molecular-weight protein in the colorimetric sensor of the invention is a peptide consisting of 3–20 amino acid residues which undergoes an antigen-antibody reaction with an antibody contained in a sample. In still another preferred embodiment, the reduced-molecular-weight protein in the colorimetric sensor of the invention is a combination of a single-stranded DNA of 100 bases or less which hybridizes with single-stranded DNA contained in a sample to form a double-stranded DNA, and an antibody which reacts with the double-stranded DNA but does not react with the single-stranded DNA contained in the sample.

The invention also provides a method for analysis of a biosample, which comprises contacting the abovementioned colorimetric sensor with a solution sample and utilizing an absorption measurement or a visual observation with the naked eye to detect color change in the polydiacetylene membrane.

The sensor of the present invention which comprises a polydiacetylene membrane is suitable for wide use and allows highly sensitive and simple detection of various ligands including ligands (analytes) which cannot be detected by the prior art. The colorimetric sensor of the invention can be manufactured easily under similar conditions for different target ligands.

EMBODIMENTS OF THE INVENTION

Figure 1:
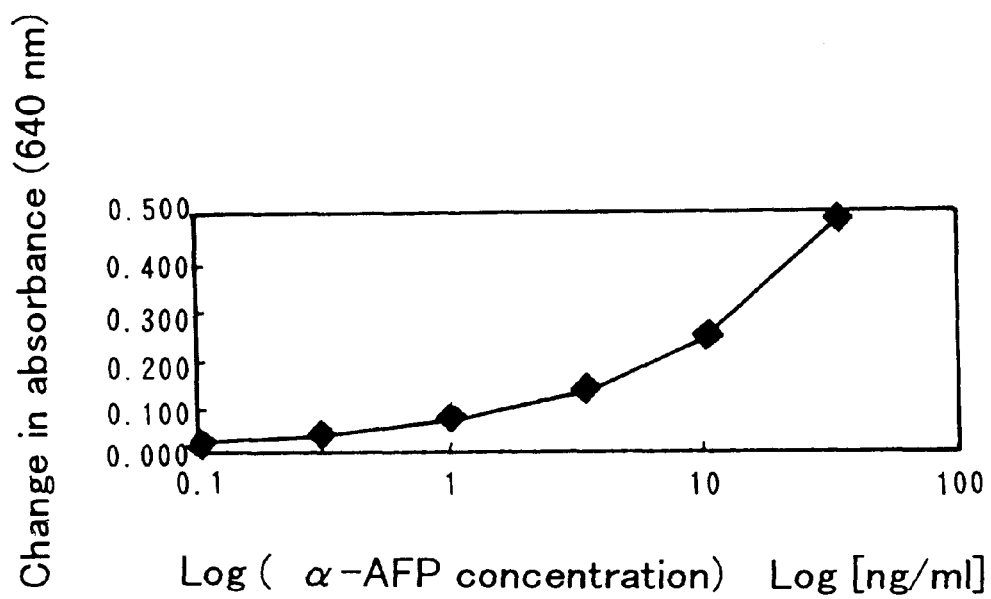
FIG. 1 is a graph showing the results of a detection test for α-AFP using the polydiacetylene membrane liposomes according to the invention.

The sensor of the invention enables highly sensitive detection of different analytes (ligands) by incorporating reduced-molecular-weight proteins (antibody proteins, antigen proteins, peptides, or nucleic acid/antibody proteins) into polydiacetylene membranes. That is, the invention is based on the finding that the incorporation of a protein of relatively low molecular weight into a polydiacetylene membrane so as to confer a structural change in the polydiacetylene membrane of such an extent which does not cause a color change, allows a very dramatic change to occur in the structure of the complex protein formed by the antigen-antibody reaction when the protein reacts with the analyte, thus allowing highly sensitive detection of disturbance of the polydiacetylene membrane structure and the resulting color change, without introducing any structural change promoter.

The sensor of the invention can be applied to any desired type of analysis system based on an antigen-antibody reaction. For example, detection of all ligands, including those which cannot be detected by the prior art since their receptors have not been identified, becomes possible by preparation of their antibodies (antibodies can be prepared for any type of ligand). Even in cases where the detailed binding structure between the antibody and its receptor has not been elucidated, the antibody can be detected by incorporating into a polydiacetylene membrane an antigenic protein or antigenic peptide known to undergo an antigen-antibody reaction with the antibody. The sensor of the invention can also be applied for detection of nucleic acids by a nucleic acid/antibody combination as will be explained later.

The sensor of the invention which is based on an antigen-antibody reaction can be manufactured by incorporating a protein into liposomes or a film made from a polydiacetylene membrane, or into a polydiacetylene membrane coated on fine particles, in a simple and stable fashion under virtually the same conditions even for different target analytes, with the protein incorporated in a quantitative manner.

For example, a liposome-type sensor according to the invention can be manufactured in all cases by forming a diacetylene membrane in an appropriate organic solvent and then removing the organic solvent, stirring the resulting diacetylene membrane with a predetermined amount of the protein in an appropriate buffer solution and subjecting the mixture to ultrasonic treatment followed by UV irradiation, to obtain a polydiacetylene membrane incorporated with the protein. A sensor of the type wherein the protein is incorporated in a polydiacetylene membrane coated onto fine particles can be obtained by carrying out the same procedure with addition of appropriate fine particles to the buffer solution.

A sensor composed of a polydiacetylene membrane film can be obtained by forming a film by the conventional LB (Langmuir-Blodgett) process, transferring it onto an appropriate support and then immersing the support with the film in a solution (buffer solution) containing a predetermined amount of the protein and subjecting the film to UV irradiation.

The examples of diacetylene used for preparing polydiacetylene membranes of the sensor of the invention are diacetylene compounds such as 10,12-pentacosadiynoic acid, 10,12-heptacosadiynoic acid and 10,12-tricosadiynoic acid, preferably in combination with diacetylene compounds having functional groups which bind to the proteins to be incorporated therein, such as 10,12-pentacosadiynoic acid N-hydroxysuccinimide ester, 10,12-heptacosadiynoic acid N-hydroxysuccinimide ester and 10,12-pentacosadiynoic acid p-nitrophenyl ester.

Thus, the sensor of the invention can be manufactured by the abovementioned procedure basically for any type of analysis system, thus avoiding the trouble of having to conduct studies to determine different preparation conditions for polydiacetylene membranes for different target ligands (analytes).

One of the outstanding advantages of the sensor of the invention is that incorporating an antibody into the polydiacetylene membrane allows the detection of substantially all naturally occurring ligands. This is because antibodies for ligands (analytes) to be detected can be easily obtained by immunizing animals using the ligands as antigens, according to conventional methods. The antibodies used may be polyclonal or monoclonal antibodies, depending on the purpose. The antibody used must be reduced to a sufficiently low molecular weight so as to not cause a color change when incorporated into the polydiacetylene membrane. Although in some cases the entire antibody can be used in the sensor of the invention, it is generally preferred to use an antibody fragment such as intact IgG, $F(ab')_2$, Fab', etc. Fab' fragments are particularly preferred because of their low molecular weight.

Sensors of the invention can detect specific antibodies by incorporating into polydiacetylene membranes various proteins or peptides known to undergo antigen-antibody reactions with those antibodies. In order to prevent color change in the polydiacetylene membrane when the protein is incorporated into the membrane, it is generally preferred for the protein to have a molecular weight of 100,000 or less, or for the peptide to consist of 3–20 amino acids. Examples of proteins and peptides which may be used in the sensor of the invention include the envelope protein (gp 120) fragment 254–274 for use in detecting HIV (human immunodeficiency virus) antibody and the envelope protein (gp 90) for use in detecting HCV (hepatitis C virus) antibody.

The sensor of the invention may also be applied for detection of nucleic acids. For example, by incorporating into the polydiacetylene membrane a single-stranded DNA (usually of 100 base pairs or less) which hybridizes with single-stranded DNA contained in a sample to form a double-stranded DNA, and an antibody which reacts with the double-stranded DNA but not with the single-stranded DNA in the sample, it is possible to achieve highly sensitive detection of DNA complementary to the DNA incorporated in the diacetylene membrane. With this sensor, the problem that color change of the polydiacetylene membrane cannot be achieved by simple formation of double-stranded DNA is solved by jointly using an antibody which reacts specifically with the double-stranded DNA. Such double-stranded DNA-specific antibodies can also be easily prepared by immunizing suitable animals with the double-stranded DNA.

By using the sensor of the invention it is possible to qualitatively and quantitatively analyze various ligands (pathogenic bacteria, viruses, toxins, etc. and active components derived therefrom, as well as physiologically active substances) in organisms based on the color change caused by the antigen-antibody reaction between the protein incorporated in the polydiacetylene membrane and the ligand (analyte) in the sample to be tested as explained above. While the analysis is generally accomplished by a measurement of the absorbance using a spectrophotometer, it may also be accomplished by a visual observation with the naked eye if qualitative analysis is the main purpose. Particularly in cases where a film-type sensor is used, the film may be mounted on a suitable support such as paper or a thin plastic sheet and immersed in a solution sample as in a litmus test, so that the presence of the target component may be easily indentified by the degree of coloration (color change).

When the sensor of the invention is to be used for quantitative analysis, it is usually used in the form of fine particles coated with the polydiacetylene membrane, for better ease of handling and sensitivity. Preferred examples of such fine particles are polystyrene, polyfluorine resins and the like. The size of the fine particles is generally preferred to be 0.01–1.0 μ m.

EXAMPLES

Examples will now be provided in order to further clarify the features of the invention, but the invention is in no way restricted by these examples.

Example 1
Incorporation of Reduced-molecular-weight Anti-human α-fetoprotein Antibody Fab' into Diacetylene/NHS-diacetylene (1:1) Membrane Liposomes, and High-sensitivity Detection of Specific Antigen.

Diacetylene (10,12-pentacosadiynoic acid, commercially available from Wako Junyaku Kogyo, KK.)and NHS-diacetylene (10,12-pentacosadiynoic acid N-hydroxysuccinimide ester, commercially available from Peptide Research Laboratories, Inc.) (1:1) were dissolved in 100 ml of an organic solvent of chloroform: methanol=2:1 to a concentration of 0.1–2 mg/ml, and after placing the solution in a 500-ml volume glass flask, the organic solvent was removed at 25° C. while rotating the flask so as to form a uniform diacetylene membrane on the glass surface. Upon adding 50 ml of a Tris-HCl buffer solution (pH 8.0) containing anti-human α-fetoprotein Fab' at 1–20 μg/ml concentration, the mixture was vigorously stirred for 10 minutes and subjected to ultrasonic treatment for homogenizing the solution to yield 50 ml of diacetylene/NHS-diacetylene (1:1) membrane liposomes incorporated with the anti-human α-fetoprotein antibody Fab'. This was subjected to UV irradiation to polymerize the diacetylene/NHS-diacetylene (1:1).

Various concentrations of α-fetoprotein (α-AFP) (0.1–100 ng/ml) were added to 1 ml aliquots of the 0.2 mg/ml liposome solution, and the change in absorbance at 640 nm was measured with a spectrophotometer (DV-640 ultraviolet/visible spectroanalyzer system, Beckman Co.).

The results are shown in Table 1 and FIG. 1, which indicate quantitative and notable changes in the absorbance over a wide range at very low concentrations of the ligand.

TABLE 1

| α-AFP concentration (ng/ml) | Change in absorbance |
|---|---|
| 0 | 0.000 |
| 0.1 | 0.015 |
| 0.3 | 0.028 |
| 1.0 | 0.061 |
| 3.3 | 0.118 |
| 10 | 0.232 |
| 33 | 0.478 |
| 100 | |

Example 2
Incorporation of Reduced-molecular-weight Anti-human α-fetoprotein Antibody Fab' into Diacetylene/NHS-diacetylene (1:1) Membrane-coated Fine Particles, and High-Sensitivity Detection of Specific Antigen.

Diacetylene/NHS-diacetylene (1:1) was dissolved in 100 ml of a solvent of chloroform: methanol=2:1 to a concentration of 0.1–10 mg/ml, and after placing the solution in a 500-ml volume glass flask, the organic solvent was removed at 25° C. while rotating the flask so as to form a uniform diacetylene membrane on the glass surface. Upon simultaneously adding 45 ml of a Tris-HCl buffer solution (pH 8.0) containing anti-human α-fetoprotien Fab ' at a 10–200 μ g/ml concentration and 5 ml of a 0.5% (w/w) solution of polystyrene latex particles with a particle size of 0.212 μm (Seradyne, U.S.), the mixture was vigorously stirred for 10 minutes and subjected to ultrasonic treatment for 3 minutes for thorough dispersion of the suspension, to yield 50 ml of diacetylene/NHS-diacetyline (1:1) membrane-coated polystyrine latex particles incorporated with the anti-human α-fetoprotien Fab'. This was subjected to UV irradiation to polymerize the diacetylene/NHS-diacetylene (1:1). The latex suspension was diluted 100-fold with water and various concentrations of human α-fetoprotein (α-AFP) (10–1000 pg/ml aliquots of the diluted suspension, and the change in absorbance at 640 nm was measured with th spectrophotometer.

Figure 2:
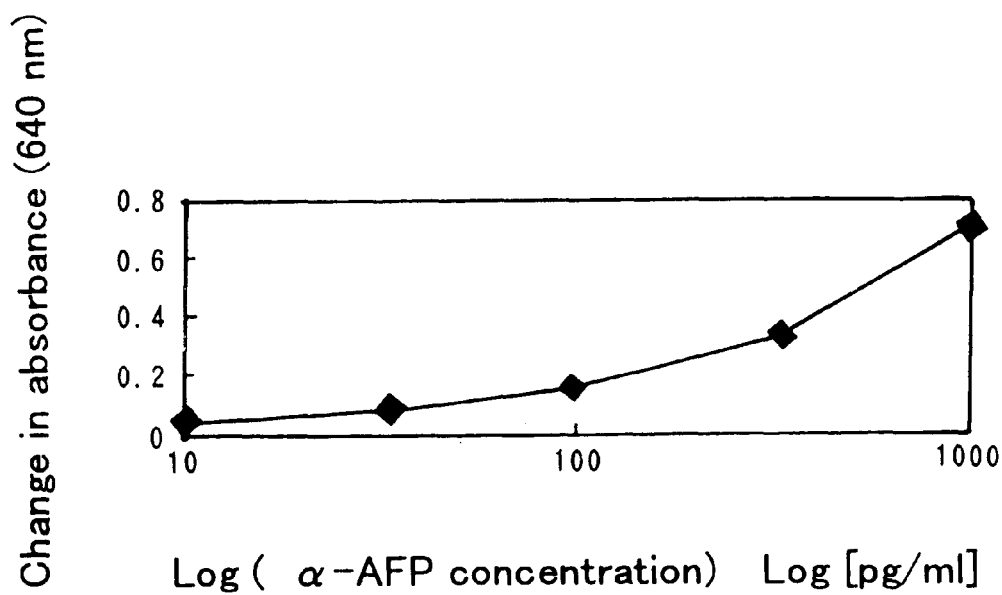
FIG. 2 is a graph showing the results of a detection test for α-AFP using the polydiacetylene membrane-coated polystyrene latex particles according to the invention.

The results are shown in Table 2 and FIG. 2, which clearly demonstrate a highly sensitive quantitative analysis.

TABLE 2

| α-AFP concentration (pg/ml) | Change in absorbance |
|---|---|
| 0 | 0.000 |
| 10 | 0.040 |
| 33 | 0.082 |
| 100 | 0.162 |
| 330 | 0.331 |
| 1000 | 0.701 |

Example 3

Incorporation of Reduced-molecular-weight Anti-human Fetoprotein Antibody Fab' into Diacetylene/NHS-diacetylene (1:1) Membrane film, and High-sensitivity Detection of Specific Antigen.

Diacetylene/NHS-diacetylene (1:1) was dissolved in 100 ml of a solvent of chloroform:methanol=2:1to a concentration of 0.1–10.0 mg/ml and the solution was spread with a Langmuir-Blodgett film-forming apparatus. The resulting film was then transferred onto a glass coated with octyl-trichlorosilane. The diacetylene/NHS-diacetylene (1:1) membrane (a film of 0.7×2.5 cm) was immersed in a 0.1 M phosphate buffer solution (pH 8.0) containing the anti-human α-fetoprotein antibody Fab' at a concentration of 1 mg/ml and reacted at 4° C. for one hour to prepare a diacetylene/NHS-diacetylene (1:1) membrane incorporated with the anti-human α-fetoprotein antibody Fab'. This was then polymerized by UV irradiation. Films prepared in this manner were then exposed to 20 μl of 0.1 M phosphate buffer containing human α-fetoprotein (α-AFP) at various concentrations (0.1–100 μg/ml concentrations), and changes in color were visually observed with the naked eye.

The results are shown in Table 3, which clearly demonstrate that qualitative analysis of extremely low concentrations is possible by the visual observation with the naked eye.

TABLE 3

| α-AFP concentration (ng/ml) | Change in color |
| --- | --- |
| 0 (buffer alone) | no |
| 0.1 | yes |
| 0.33 | yes |
| 1.0 | yes |
| 3.3 | yes |
| 10 | yes |
| 33 | yes |
| 100 | yes |

Example 4
Incorporation of HIV Envelope Protein (gp 120) Fragment 254–274 SEQ. I.D. NO. 1 (Cys-Thr-His-Gly-Ile-Arg-Pro-Val-Val-Ser-Thr-Gln-Leu-Leu-Leu-Asn-Gly-Ser-Leu-Ala-Glu) into Diacetylene Membrane Liposomes, and High-sensitivity Detection of HIV Antibody.

Figure 3:
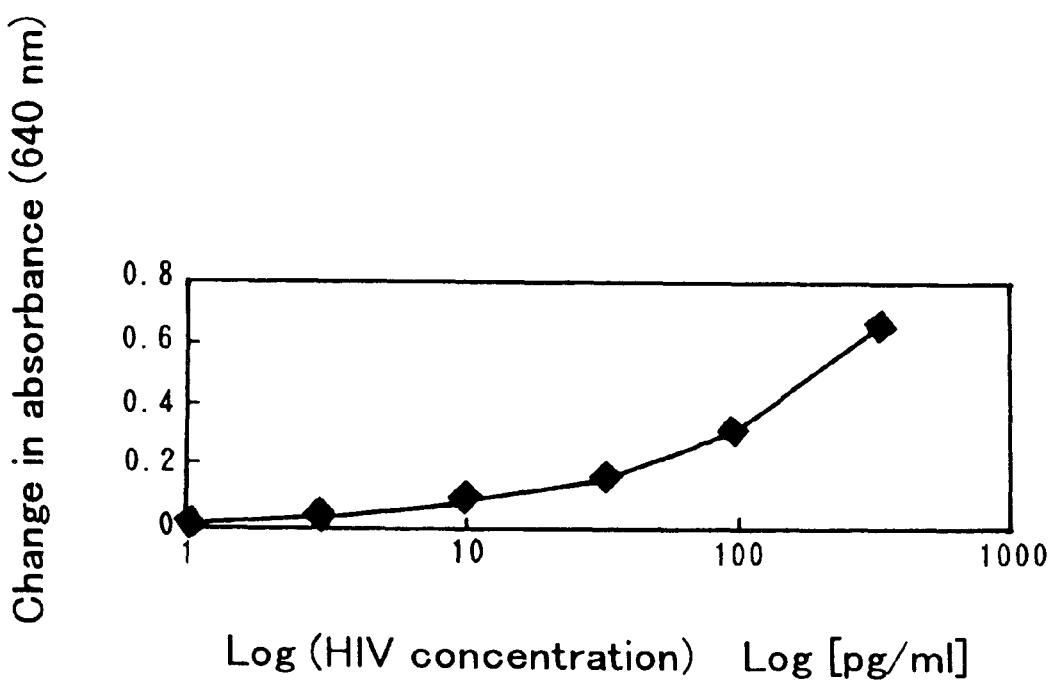
FIG. 3 is a graph showing the results of a detection test for HIV antibody using the polydiacetylene membrane liposomes according to the invention.

Diacetylene was dissolved in 100 ml of an organic solvent of chloroform:methanol=2:1 to a concentration of 0.1–2 mg/ml, and after placing the solution in a 500-ml volume glass flask, the organic solvent was removed at 25 ° C. while rotating the flask so as to form a uniform diacetylene/NHS-diacetylene (1:1) membrane on the glass surface. Upon adding 50 ml of a Tris-HCl buffer solution (pH 8.0) containing the HIV envelope protein (gp 120) fragment 254–274 (Sigma Aldrich Japan) at a 1–20 $\mu$ g/ml concentration, the mixture was vigorously stirred for 10 minutes and subjected to ultrasonic treatment for homogenizing the solution to yield 50 ml of diacetylene/NHS-diacetylene (1:1) membrane liposomes incorporated with the HIV envelope protein (gp 120) fragment 254–274. This was subjected to UV irradiation to polymerize the diacetylene. Various concentrations of inactivated HIV (0.1–1000 pg/ml) were added to 1 ml aliquots of the 0.2 mg/ml liposome solution, and the change in absorbance at 640 nm was measured with a spectrophotometer (DV-640 ultraviolet/visible spectroanalyzer system, Beckman Co.). The results are shown in Table 4 and FIG. 3.

TABLE 4

| HIV concentration (pg/ml) | Change in absorbance |
| --- | --- |
| 0 | 0.000 |
| 1.0 | 0.018 |
| 3.0 | 0.032 |
| 10 | 0.078 |
| 33 | 0.152 |
| 100 | 0.311 |
| 330 | 0.641 |
| 1000 | |

Example 5
Incorporation of HIV Envelope Protein (gp 120) Fragment 254–274 SEQ. I.D. NO. 1 (Cys-Thr-His-Gly-Ile-Arg-Pro-Val-Val-Ser -Thr-Gln-Leu-Leu-Leu-Asn-Gly-Ser-Leu-Ala-Glu) into Diacetylene (1:1) Membrane-coated Fine Particles, and High-sensitivity Detection of HIV Antibody.

Figure 4:
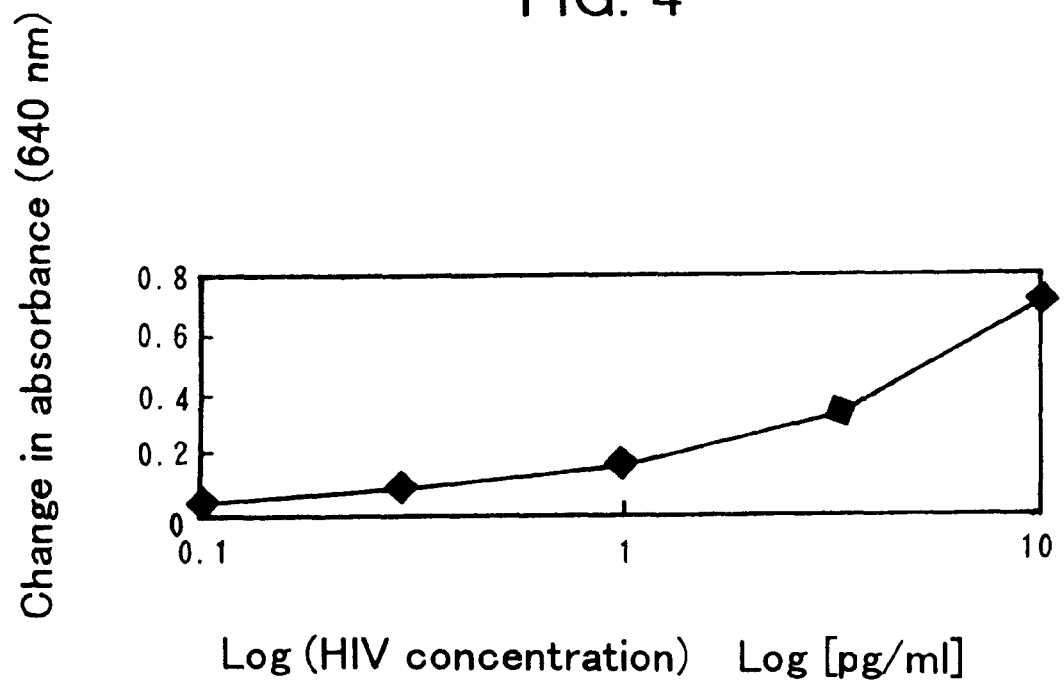
FIG. 4 is a graph showing the results of a detection test for HIV antibody using the polydiacetylene membrane-coated polystyrene latex particles according to the invention.

Diacetylene/NHS-diacetylene (1:1) was dissolved in 100 ml of a solvent of chloroform:methanol=2:1 to a concentration of 0.1–10 mg/ml, and after placing the solution in a 500 –ml volume glass flask, the organic solvent was removed at 25° C. while rotating the flask so as to form a uniform diacetylene membrane on the glass surface. Upon simultaneously adding 45 ml of a 0.1 M phosphate buffer solution (pH 7.5) containing the HIV envelope protein (gp 120) fragment 254–274 at a 1–200 $\mu$ g/ml concentration and 5 ml of a 0.5% (w/w) solution of polystyrene latex particles with a particle size of 0.212 $\mu$ m (Seradyne, U.S.), the mixture was vigorously stirred for 10 minutes and subjected to ultrasonic treatment for 3 minutes for thorough dispersion of the suspension, to yield 50 ml of diacetylene/NHS-diacetylene (1:1) membrane-coated polystyrene latex particles incorporated with the HIV envelope protein (gp 120) fragment 254–274. This was subjected to UV irradiation to polymerize the diacetylene/NHS-diacetylene (1:1). The latex suspension was diluted 100-fold with water and various concentrations of inactivated HIV (0.1–10 pg/ml) were added to 1 ml aliquots of the diluted suspension, and the change in absorbance at 640 nm was measured with the spectrophotometer. The results are shown in Table 5 and FIG. 4.

TABLE 5

| HIV concentration (pg/ml) | Change in absorbance |
| --- | --- |
| 0 | 0.000 |
| 0.1 | 0.040 |
| 0.3 | 0.082 |
| 1.0 | 0.162 |
| 3.3 | 0.331 |
| 10 | 0.701 |

Example 6
Incorporation of HIV Envelope Protein (gp 120) Fragment 254–274 SEQ. I.D. NO. 1 (Cys-Thr-His-Gly-Ile-Arg-Pro-Val-Val-Ser-Thr-Gln-Leu-Leu-Leu-Asn-Gly-Ser-Leu-Ala-Glu) into Diacetylene/NHS-diacetylene (1:1) Membrane Film, and High-sensitivity Detection of HIV Antibody.

Diacetylene/NHS-diacetylene (1:1) was dissolved in 100 ml of a solvent of chloroform:methanol=2:1 to a concentration of 0.1–10.0 mg/ml and the solution was spread with a Langmuir-Blodgett film-forming apparatus. The resulting film was then transferred onto a glass coated with octyltrichlorosilane. The diacetylene/NHS-diacetylene (1:1) membrane (a film of 0.7×2.5 cm) was immersed in a 0.1 M phosphate buffer solution (pH 8.0) containing the HIV envelope protein (gp 120) fragment 254–274 at a concentration of 1 mg/ml and allowed for the reaction at 4° C. for one hour to yield a diacetylene/NHS-diacetylene (1:1) membrane incorporated with the HIV envelope protein (gp 120) fragment 254–274. This was then polymerized by UV irradiation. Films were then exposed to 20 $\mu$ l of 0.1 M phosphate buffer containing the HIV envelope protein (gp 120) fragment 254–274 at various concentrations (10–10, 000 pg/ml), and changes in color were visually observed with the naked eye. The results are shown in

TABLE 6

| HIV concentration (ng/ml) | Change in color |
| --- | --- |
| 0.0 (buffer alone) | no |
| 10 | yes |
| 33 | yes |
| 100 | yes |

TABLE 6-continued

| HIV concentration (ng/ml) | Change in color |
|---|---|
| 330 | yes |
| 1000 | yes |
| 3300 | yes |
| 10000 | yes |

Example 7
Incorporation of Deoxyribonucleotides (DNA) into Polydiacetylene Membrane and Simple High-sensitivity Detection of Specific DNA in Specimens.

To polydiacetylene membrane films prepared according to the method described in Example 3 and incorporated with amounts (0.1–100 pg) of the probe DNA (number of base pairs: 20 mers, SEQ. I.D. NO. 1 TATGCTTCCGGCTCGTATGT), there were added 20 μl each of a solution sample containing the complementary DNA SEQ. I.D. NO. 3 (ATACGAAGGCCGAGCATACA). No color change was not observed. Next, 20 μl of a solution containing an antibody (10 μg/ml) which reacts only with the double-stranded DNA was added to each film, and the change in color after 60 seconds was visually observed.

The results are shown in Table 7. The results in Table 7 demonstrate that DNA in the samples can be easily and rapidly detected at a high sensitivity by using an antibody which reacts specifically with the double-stranded DNA.

TABLE 7

| Amount of specimen DNA (pg) | Color change before addition of antibody for dsDNA | Color change after addition of antibody for dsDNA |
|---|---|---|
| 0 | no | no |
| 0.1 | no | yes |
| 0.3 | no | yes |
| 1.0 | no | yes |
| 3.3 | no | yes |
| 10 | no | yes |
| 33 | no | yes |
| 100 | no | yes |

What is claimed is:

1. A colorimetric sensor comprising polydiacetylene membrane liposomes, a polydiacetylene membrane film or fine particles coated with a polydiacetylene membrane, in which said polydiacetylene membrane is incorporated with a protein having a reduced molecular weight low enough not to cause color change in the polydiacetylene membrane, wherein said reduced-molecular-weight protein is a combination of single-stranded DNA of 100 bases or less which hybridizes with single-stranded DNA contained in a sample to form a double-stranded DNA, and an antibody which reacts with said double-stranded DNA but does not react with the single-stranded DNA contained in the sample.

* * * * *